US007226342B2

(12) United States Patent
Hertz (10) Patent No.: US 7,226,342 B2
(45) Date of Patent: Jun. 5, 2007

(54) HANDHELD APPARATUS FOR DELIVERY OF PARTICULATE MATTER WITH DIRECTIONAL FLOW CONTROL

(76) Inventor: Reuben Hertz, 2318 Sea Island Dr., Fort Lauderdale, FL (US) 33301

( * ) Notice: Subject to any disclaimer, the term of this patent is extended or adjusted under 35 U.S.C. 154(b) by 0 days.

(21) Appl. No.: 09/939,865

(22) Filed: Aug. 27, 2001

(65) Prior Publication Data

US 2002/0002030 A1 Jan. 3, 2002

Related U.S. Application Data

(63) Continuation-in-part of application No. 09/196,498, filed on Nov. 21, 1998, now Pat. No. 6,287,180, and a continuation-in-part of application No. 08/517,379, filed on Aug. 21, 1995, now Pat. No. 5,839,946.

(51) Int. Cl.
   *B24C 5/02* (2006.01)
(52) U.S. Cl. ......................... 451/90; 451/102
(58) Field of Classification Search ............... 451/102, 451/90, 38, 99, 39, 101
   See application file for complete search history.

(56) References Cited

U.S. PATENT DOCUMENTS

| 2,133,149 A | 10/1938 | Poncelet |
| 2,441,441 A | 5/1948 | Paasche |
| 2,577,465 A | 12/1951 | Jones et al. |
| 2,612,732 A | 10/1952 | Ziegler |

(Continued)

FOREIGN PATENT DOCUMENTS

GB 832231 4/1960

OTHER PUBLICATIONS

AeroEtcher Blaster Advertisement.

(Continued)

*Primary Examiner*—Robert A. Rose
(74) *Attorney, Agent, or Firm*—Allen D. Hertz (57) ABSTRACT

A disposable apparatus for propelling particulate matter against a surface of a target material that includes: a mixing chamber having a chamber wall, a multi-conduit receiving port, a propellant-gas receiving conduit, and a discharge conduit. The gas delivery conduit extends from the propellant-gas receiving port into the chamber, a mixture discharge conduit extending from the mixture discharge port into the chamber, and a quantity of particulate matter inside the chamber. The disposable apparatus further includes a membrane capable of allowing a gas stream to pass through when the gas stream is flowing and seals the mixing chamber when the gas stream is not flowing. The membrane can be of a hemispherical shaped, molded piece that includes at least one slit to provide an opening when the gas stream is flowing. A method is provided for propelling particulate matter against a surface of a target material using the above-described apparatus, including the steps of delivering a stream of gas into the air delivery conduit and into the mixing chamber from the gas source, so that the gas stream blows through the quantity of particulate matter, causing the particulate matter to mix with the gas stream, forming a gas and particle mixture, and discharging the mixture through the discharge conduit and the discharge port to strike the surface of the target material. The method further provides a means for automatically containing the particulate matter within the mixing chamber when the apparatus is not in use.

33 Claims, 7 Drawing Sheets

U.S. PATENT DOCUMENTS

| | | |
|---|---|---|
| 2,641,087 A | 6/1953 | Greiser |
| 2,696,669 A | 12/1954 | Ikse |
| 2,725,684 A | 12/1955 | Crowe |
| 2,744,361 A | 5/1956 | Larson et al. |
| 3,164,153 A | 1/1965 | Zorzi |
| 3,626,841 A | 12/1971 | Schachter |
| 3,631,631 A | 1/1972 | Greenstein |
| 3,964,509 A * | 6/1976 | Daubenberger et al. . 137/525.1 |
| 3,981,479 A | 9/1976 | Foster et al. |
| 4,032,474 A | 6/1977 | Goudriaan et al. |
| 4,174,571 A | 11/1979 | Gallant |
| 4,287,812 A | 9/1981 | Iizumi |
| 4,369,607 A | 1/1983 | Bruggeman et al. |
| 4,391,590 A | 7/1983 | Dougherty |
| 4,475,370 A | 10/1984 | Starke et al. |
| 4,646,782 A | 3/1987 | Ezekoye |
| 4,673,051 A | 6/1987 | Dariling et al. |
| 4,941,298 A | 7/1990 | Fernwood et al. |
| 4,967,791 A | 11/1990 | Sternberger |
| 5,123,206 A | 6/1992 | Woodson |
| 5,199,229 A * | 4/1993 | Herold et al. ............... 451/102 |
| 5,289,919 A | 3/1994 | Fisher |
| 5,330,354 A | 7/1994 | Gallant |
| 5,368,844 A | 11/1994 | Gaffar et al. |
| 5,839,946 A | 11/1998 | Hertz |
| 6,004,191 A | 12/1999 | Schur et al. |
| 6,354,924 B1 * | 3/2002 | Trafton et al. ................ 451/90 |

OTHER PUBLICATIONS

Airtouch Brochure.
Miniblaster advertisement.
StarDental—Startech Air Abrasion System Brochure.
PREP Tech Cp1 Air Abrasion Brochure.
Mirage Dental Handiblaster Brochure.
Crystal Air Air Abrasion advertisement.
CRA Newsletter.
Abradent Ultralow Air Abrasion Device.
Prep Start Air Abrasion Cavity Prep.
Parkell Corp., Product "Eraser Air Polishing Prophy Pencil" Advertisement.
Sullivan / Schein Dental Corp., Product "Minipolisher" Article.
Dentsply Preventative Care, Product "SPS Scaler & Jet" Brochure.
American Dental Technologies advertisement.
Airtechniques Airdent II Brochure.
Airtechniques AirDent II CS Brochure.

* cited by examiner

HANDHELD APPARATUS FOR DELIVERY OF PARTICULATE MATTER WITH DIRECTIONAL FLOW CONTROL

It is still another object of this invention to provide a device for precise delivery of a fluid particle stream that is pre-charged with particulate abrasive matter.

It is still yet another object of this invention to provide a device for precise delivery of a fluid particle strewn which includes an adjustable dispensing conduit, or nozzle, for directing the flow of the fluid particle stream onto a delimited area of a target surface.

It is an additional object of this invention to provide a device for precise delivery of a fluid particle stream which includes means for introduction of the stream of fluid, under pressure, into a mass of abrasive particles within the device so as to create a turbulent mixture thereof that can be discharged via a dispensing conduit or nozzle onto a delimited area of a target.

It is a yet additional object of his invention to provide a method for precise delivery of a fluid particle stream to effect selective abrasion of a delimited area of a target.

SUMMARY OF THE INVENTION

The above and related objects are achieved by providing a device for the precision delivery of a particle stream of abrasive material to a delimited area of a target. In one of the preferred embodiments of the invention, the device comprises an essentially closed chamber having a fitting that is adapted for releasable connection to a source of pressurized fluid means for directing the pressurized fluid into a mass of abrasive particles within the closed chamber so as to generate a mixture of fluid and abrasive particles within the closed chamber and a nozzle for delivery of the fluid and particle mixture to a delimited area of a target. The term "fluid" as used herein is intended as inclusive of gases, liquids and any combination thereof. In the preferred embodiments of this invention, the source of gas is an air compressor, or pressurized canister containing & or an inert gas. The abrasive particles, which are suitable for use in this device, include aluminum oxide, sodium bicarbonate and other common polishing or grinding agents. The particle size of the abrasive should obviously be smaller than the any of the passages of the device through which they are to pass. The particle density is to a degree limited by the amount of pressure required to effect mixing thereof with the fluid in the chamber of the device and thereafter the transport/flow of the resultant mixture through the nozzle of the device.

The pressurized fluid is introduced into the chamber at or near the top of the device, and thereafter is directed through a fluid transport conduit to the base of the device where it is forced through a free-flowing mass of particulate (abrasive) matter that has been predisposed within the device at the time of its manufacture. Upon injection of the fluid into the chamber, turbulent mixing of fluid and abrasive particles occurs which mixture is and remains under substantial pressure (generally in excess of one (1) atmosphere). This is accomplished by control of the cross-sectional area of the fluid transport conduit relative to the cross-sectional area of the nozzle. The selection of a specific diameter for these two device components is a function of intended use, the particle size of the abrasive material to be delivery with such device and the desired force to be exerted upon the target by the fluid particle stream as it is expelled from the end of the nozzle onto the target surface. In the preferred embodiments of the invention, the cross-sectional dimension of the fluid transport conduit is greater than the cross-sectional dimension of the nozzle. More specifically, the inside diameter of the conduit designed for dental applications is preferably at least about 50% greater than the cross-sectional area of the nozzle and can range from about 0.01" to about 0.20", with the most preferred diameter being about 0.045". The inside diameter of the nozzle can range from about 0.005" to about 0.100", with the preferred diameter being about 0.021".

In the preferred embodiment of the invention the nozzle comprises an elongated tube fixedly positioned in an orifice in the base of the chamber, and which extends both into and from the base of the chamber. The degree of extension of the distal end of the nozzle into the chamber is calculated to contribute and promote the formation of a turbulent mixture of fluid and particles in the chamber; and, the proximal end of the nozzle, the precise delivery of the fluid stream containing the abrasive particles.

In one of the preferred embodiments of this invention the distal end of the nozzle is positioned near the top (lid) of the chamber, and above the open end of the fluid transport conduit. In addition, the relative height, or extension, of the nozzle into the chamber is also a function of the volume of abrasive particles that is to be pre-loaded into the chamber at the time of manufacture. More specifically, it is preferable that the height of the nozzle extend at least above the level of the anticipated abrasive charge, and yet be sufficiently distant from the top (lid) of the chamber to allow for turbulent mixing and channeling of the mixture into the opening at the distal end of the nozzle.

The chamber design of the device is further unique in that it provides an effective and inexpensive configuration for the precise delivery of a fluid particle stream in a disposable package.

This invention also provides a method for propelling particulate matter against a surface of a target material using the above-described apparatus, including the steps of delivering a stream of fluid (e.g. gas) into the fluid delivery conduit and from such conduit into the chamber of this device, so that the flow of the gas stream continuously blows through the quantity of particulate matter, causing the particulate matter to mix with the gas stream, forming a gas and particle mixture, and discharging the mixture through the discharge conduit and the discharge part to strike the surface of the target material.

BRIEF DESCRIPTION OF THE DRAWINGS

The drawings, which are provided and described herein, are intended to be illustrative of a number of the preferred embodiments of this invention. Where an element of an illustrated device is common to more than one drawing, it is assigned the same reference numeral for continuity of expression and case of understanding.

DETAILED DESCRIPTION OF THE INVENTION INCLUDING PREFERRED EMBODIMENTS

The detailed embodiments of the invention disclosed herein are representative of a number of the preferred configurations of the device.

First Preferred Embodiment

Referring to FIGS. 1–4, a disposable particle-propelling apparatus 10 is disclosed for propelling particulate matter P against target material T. The apparatus 10 includes a cylindrical mixing chamber 16 having a chamber wall 20 and two end wall portions 22 (fid) and 24 (base), respectively. Apparatus 10 is powered by a compressed gas source, such as an air compressor or a compressed gas cylinder (not shown), which connects to and is in fluid communication with the gas receiving port 26 of end wall portion 22. The gas-delivery conduit 32 extends from the gas receiving port 26 into the mixing chamber 16. End wall 24 (base) has a mixture discharge port 34. A mixture discharge conduit 28 extends in fluid communication from mixture discharge port 34 into mixing chamber 16. A particle directing tube 36 is provided in fluid communication with discharge port 34 and extends opposite discharge conduit 28 outside from mixing chamber 16- A quantity of particulate matter P is scaled inside chamber 16, the quantity being sufficient to only partially fill chamber 16, leaving space for gas and particulate water P to mix. The complete sealing of the particulate matter P gives matter P a virtually unlimited shelf life and protection from contamination (e.g. humidity). Mixing chamber 16 provides a gas-tight seal to maintain particle sterility and to prevent gas leakage during operation. An inlet cap 42 and a lip cap 44 seal gas-receiving port 26 and mixture discharge part 34, respectively, and are removed when apparatus 10 is to be connected to the compressed gas source for use. Volume grid markings 46 are preferably provided on the wall side portion 20 of chamber 16 so that the quantity of particulate matter P used can be measured and visually observed when wall 20 is constructed of a transparent or translucent material. Chamber wall 20 may also be color-coded to identify the type of particulate matter P. The color code marking CC may indicate the particle size and the type of particulate matter P. Tube 36 serves to both direct and accelerate the discharging gas and particular matter P mixture from the mixing chamber. As a result, the particulate matter P can be applied to a focused or delimited area of a target and at a uniform velocity. Since apparatus 10 is disposable, tube 36 can be fabricated inexpensively to sustain a limited use. Tube 36 is manually bendable (without crimping) thus permitting it to be quickly set to an angle without crimping, making the discharge omni-directional, and, thus, provide access to-hard-to-reach surfaces. Tube 36 preferably has a preset orifice diameter to accommodate a given size and type of particulate matter P, and is preferably made of metal, but may also be formed of suitable durable plastic or comparable material.

Figure 1:
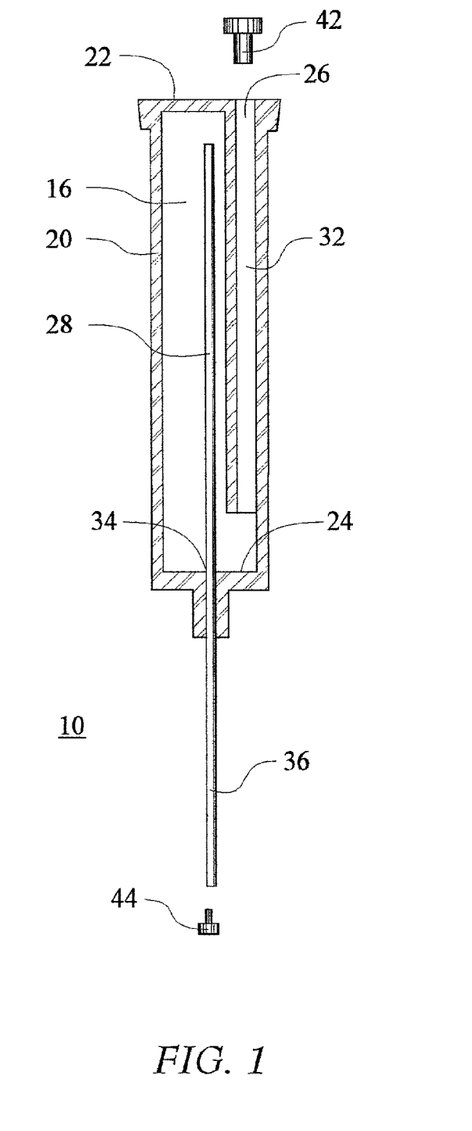
FIG. 1 is a cross-sectional side view of the preferred embodiment of the inventive particle-propelling apparatus. The particulate matter and gas source are omitted.
Figure 2:
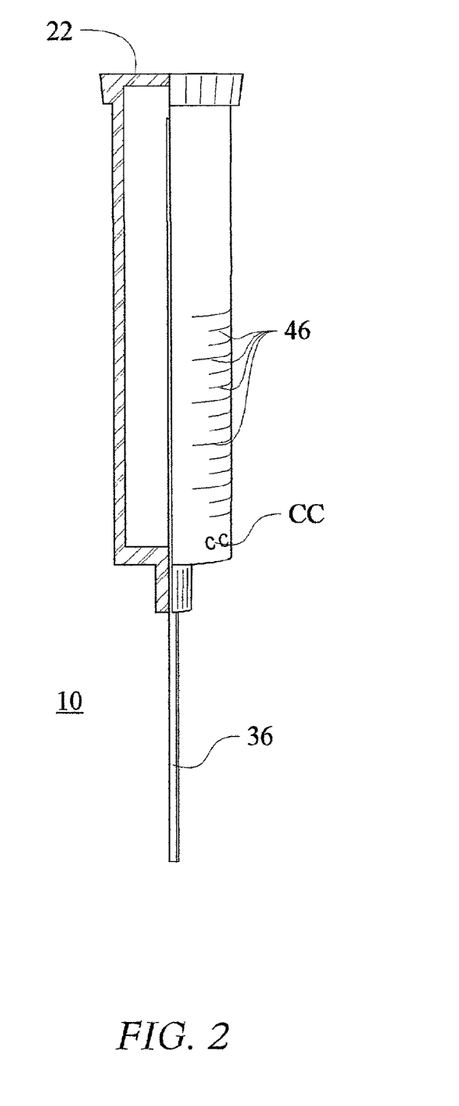
FIG. 2 is a partial cross-sectional side view of the apparatus of FIG. 1, revealing some of the outer chamber side wall loving optional grid measuring markings and a circumferential color-code band.
Figure 2A:
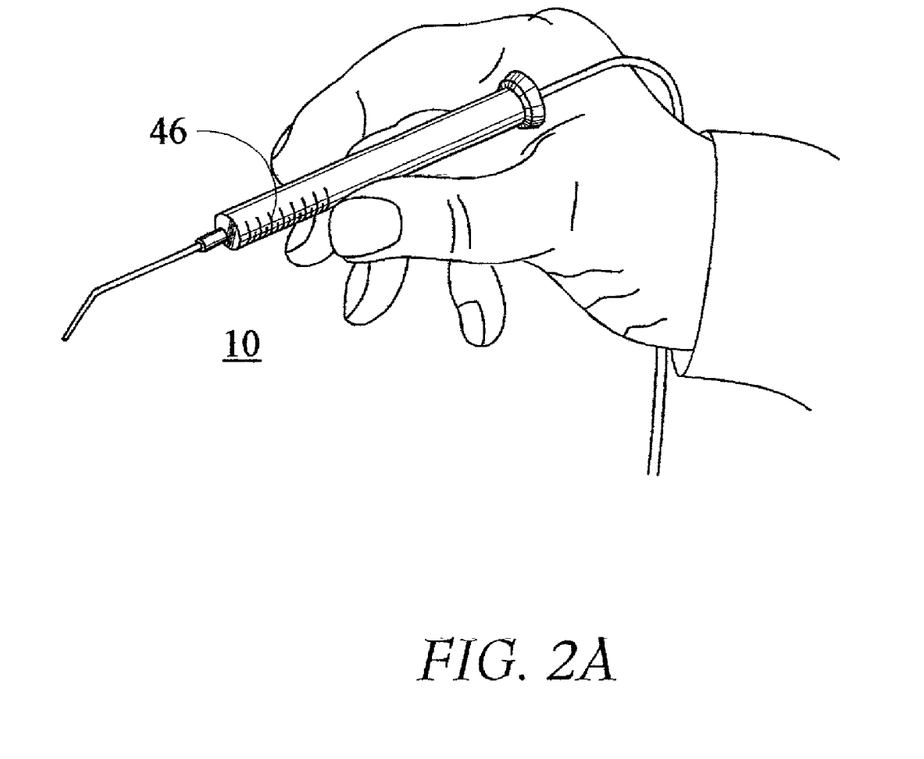
FIG. 2*a* is a perspective view of the apparatus of FIG. 2 in the hands of a user ready for operation.
Figure 3:
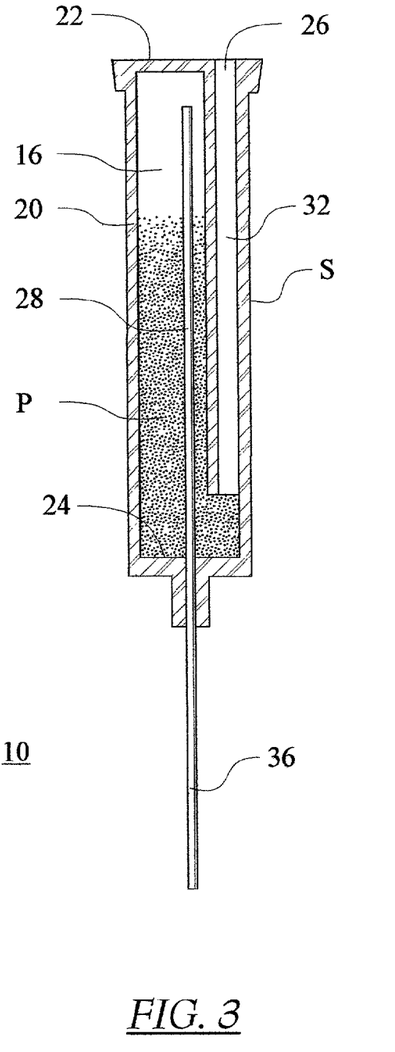
FIG. 3 is a view as in FIG. 1, showing the apparatus with the particulate matter added.
Figure 4:
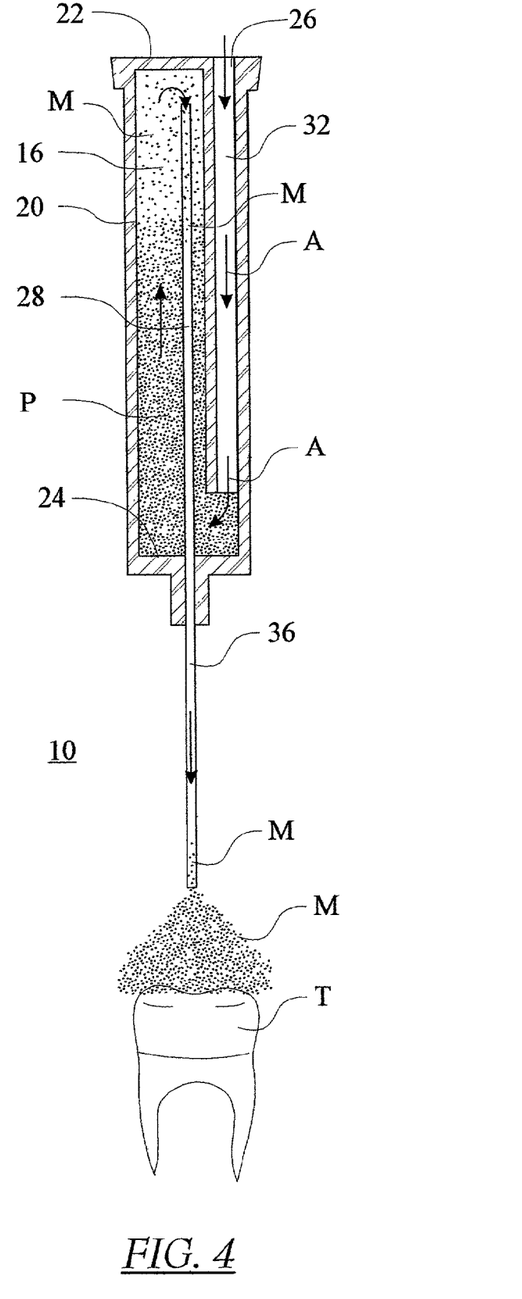
FIG. 4 is a view as in FIG. 3, with the apparatus in operation discharging the gas and particulate matter mixture toward a surface of a target material.

Chamber 16 is preferably an integrated chamber with balanced distribution of weight that is preferably slender enough to hold and manipulate as though it were a writing instrument. The direct, blow-through, turbulent mixing within chamber 16 makes apparatus 10 operational at all orientations relative to the target surface and to the direction of gravity. The slender construction makes chamber 16 able to access narrow spaces and operate in small confined areas. Chamber 16 can receive and function with varying gas pressures applied to gas-receiving port 26, selected to accelerate particles to various desired velocities for various given tasks. Turbulent mixing of particulate matters P directly in the path of the gas stream within chamber 16 enables apparatus 10 to deliver particulate matters P of a wide range of sizes, and to mix and deliver a wide range of particulate matter types. The direct, blow-through mixing in chamber 16, permits operation at very low pressures, thereby increasing the range of operational pressures that may be selected.

Apparatus 10 contains no moving parts and is preferably made of disposable plastic, so that particulate matter P and apparatus 10 can be sterilized at the factory, and apparatus 10 replaced rather than refilled and reused. Apparatus 10 is designed to with stand common sterilization techniques such as autoclave, chemical treatments and irradiation. Contemplated apparatus 10 construction materials may include but are not limited to plastic, stainless steel, Delrin™, and Teflon™. Apparatus 10 is lightweight, manufactured to be recyclable, and easy to use and replace without training or maintenance.

Figure 5:
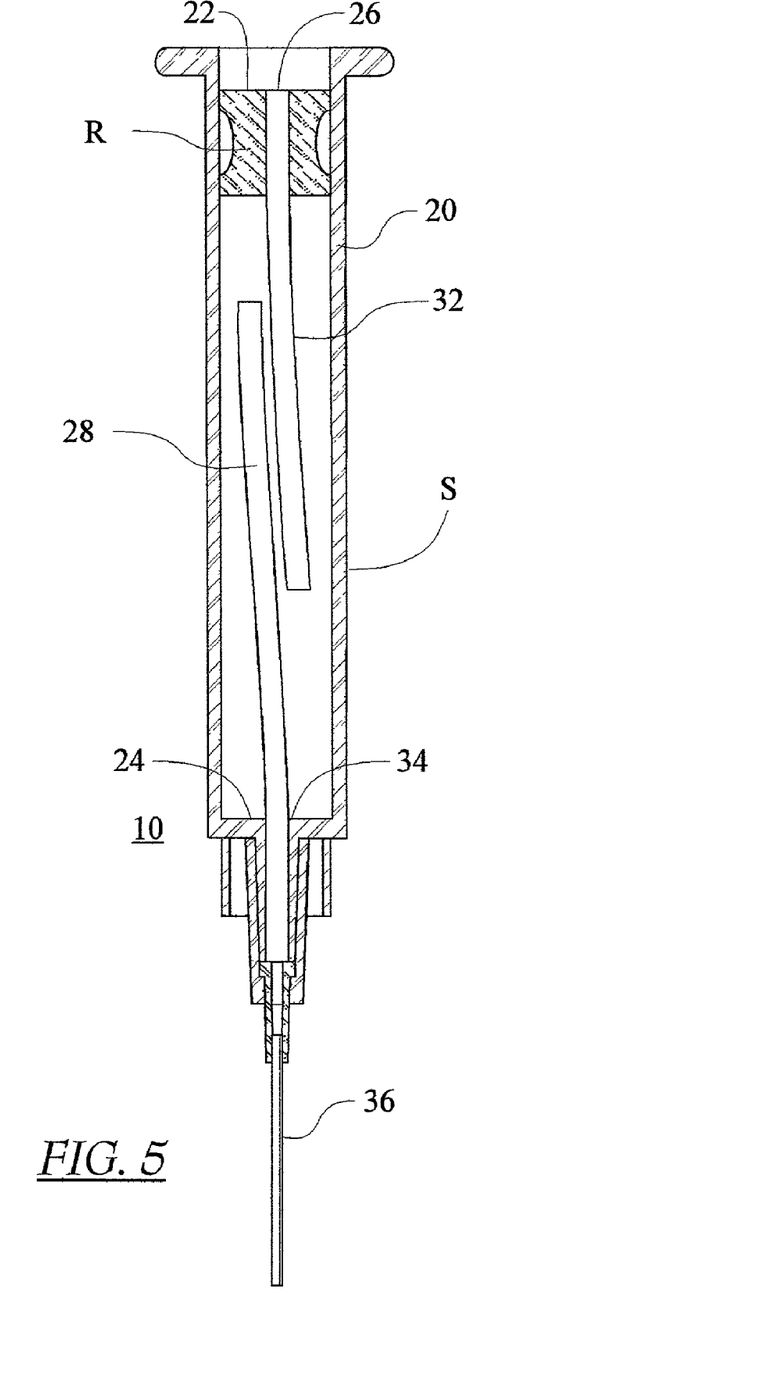
FIGS. 5 and 6 show alternative embodiments of the claimed apparatus, formed from a conventional industrial syringe.
Figure 5A:
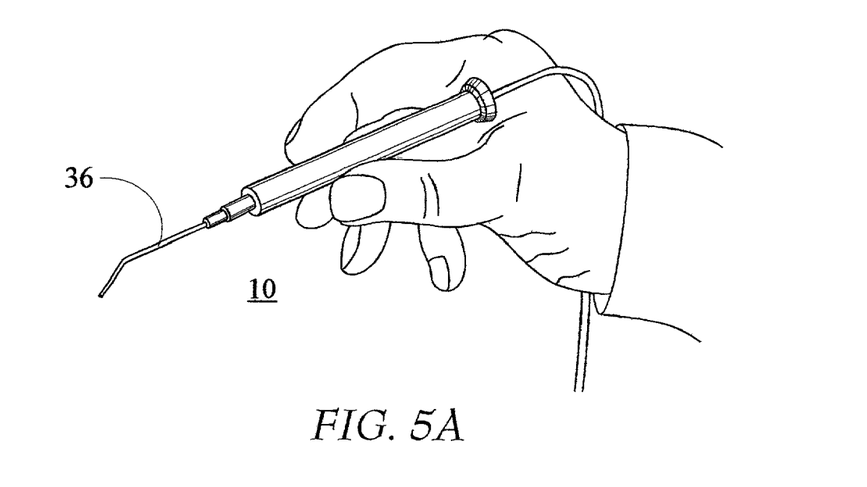
FIG. 5a is a perspective view of the apparatus of FIG. 5 in the hand of a user ready for operation.
Figure 6:
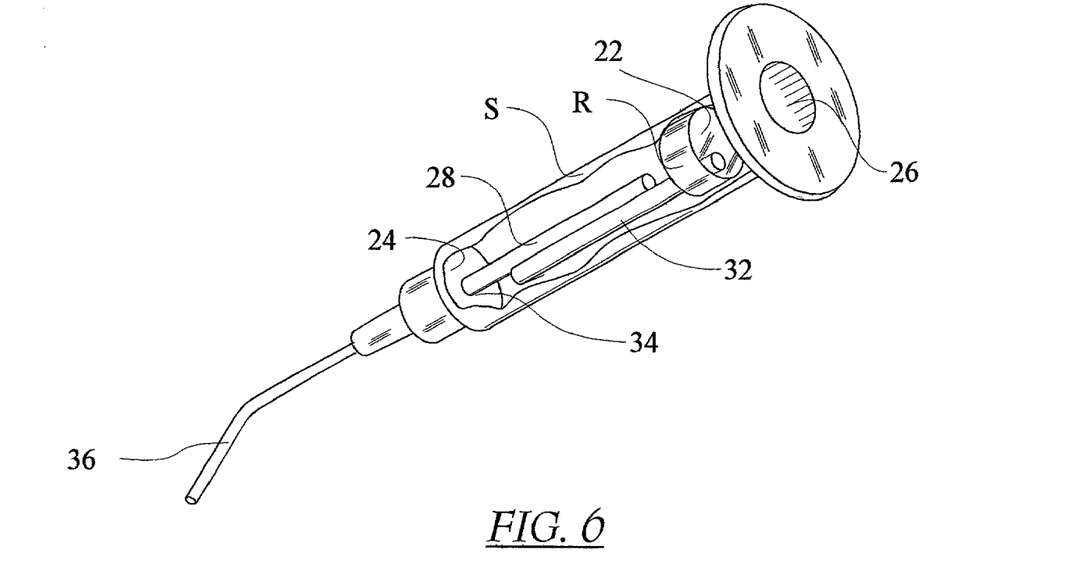

Apparatus 10 can be constructed from an adapted disposable syringe S of a type that is extremely common in the health care industry, see FIGS. 5 and 6. Needle 36 is attached to a standard syringe needle with a dulled tip, and formed of either metal or plastic. Gas-receiving port 26 is a hole bored into a standard rubber syringe stopper R separated from a standard syringe plunger. Mixture discharge port 34 is the existing discharge opening of the syringe S, while standard tubing can be used for gas delivery conduits 32 and 28.

Second Preferred Embodiment

Figure 7:
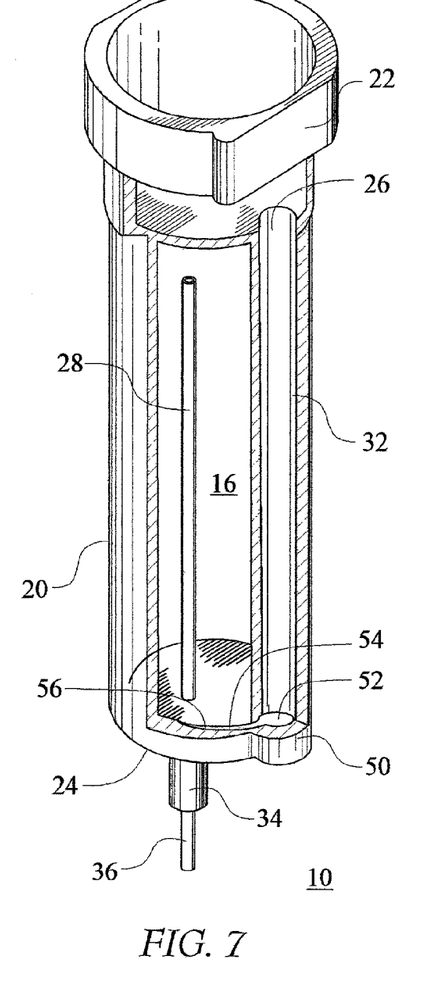
FIG. 7 is a perspective view, in partial section, of an alternative embodiment of the device of this invention in which a fluid delivery conduit is molded into the body of the device housing.

FIG. 7 depicts an alternative embodiment of the invention wherein the design choice of the various component parts thereof is based, in part, upon fabrication demands dictated by injection molding constraints and manufacturing economies. More specifically, the fluid delivery conduit (32) is fabricated as an integral component of the chamber wall (20). The fluid-deliver conduit (32) is further distinct from the First Preferred Embodiment described above in that such conduit now extends the full length of the chamber to the base (24) thereof. The base (24) is also unique in that a chute (50) (as more fully illustrated in FIG. 8 described hereinafter) has been formed therein to provide for deflection of the fluid into the chamber so as to cause effective mixing of the fluid and the particle charge into a chute formed within the base of the chamber. This chute includes three distinctive functional features, namely an essentially round or bowl-like cavity (52) that roughly corresponds in overall dimension with the distal end of the fluid-delivery conduit (32). The second functional features comprises an intermediate section (54), or ascending ramp which is characterized by its progressive slope, that extends for the round or bowl-like cavity (52) to a riser (56) which directs the fluid into the chamber and thereby turbulence and/or a vortex within the chamber so as to effect mixing of the fluid with the free flowing particles that are contained therein.

Figure 8:
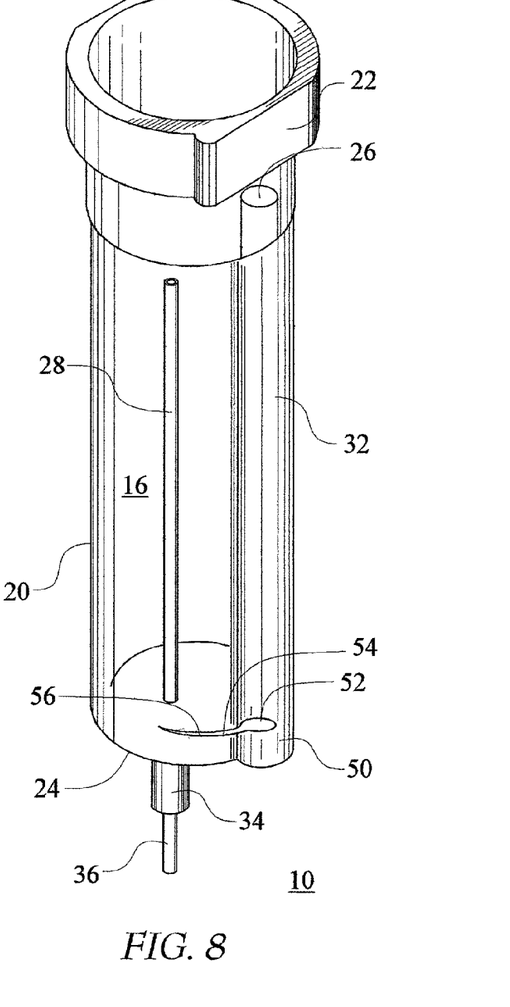
FIG. 8 is a perspective view of the device of FIG. 7 that has been molded from a transparent material.

FIG. 8 further illustrates additional detail of the construction of the device of FIG. 7 wherein the interior of the base of the device is revealed. More specifically, FIG. 8 depicts a device of the type illustrated in FIG. 7 fabricated from a plastic material. In this view, the detail of the base (24) is better revealed in that it further depicts the chute (50) and the ascending ramp (54) for channeling the fluid stream from the conduit into the chamber of the device. The chute can be modified as desired to optimize mixing and/or other operational objectives.

Molded Flow Control and Sealing Feature

Figure 9:
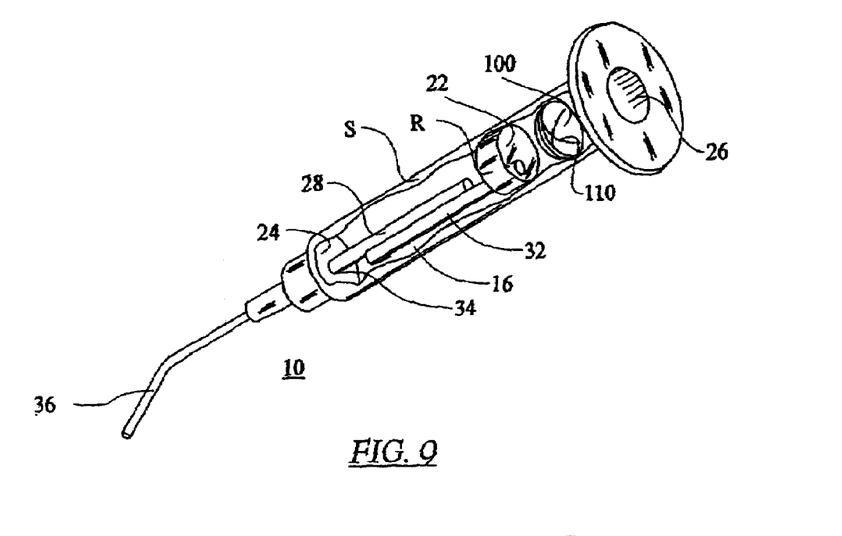
FIG. 9 is a perspective view of an apparatus including a molded, unidirectional flow control apparatus.
Figure 10:
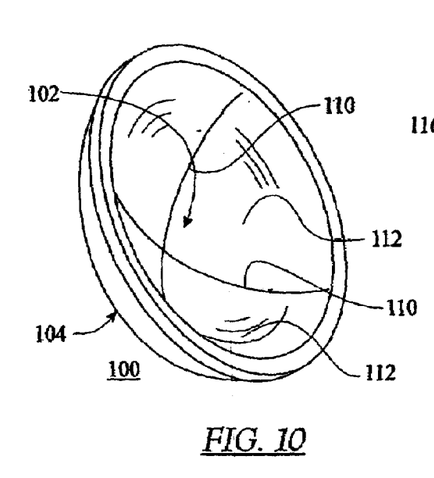
FIG. 10 is a detailed perspective view of the molded, unidirectional flow control apparatus.
Figure 10A:
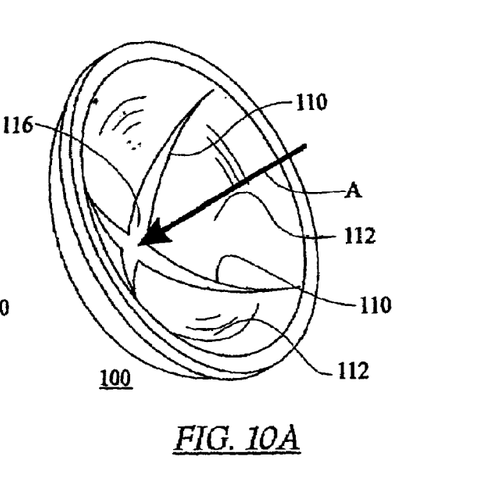
FIG. 10A is a detailed perspective view of the molded, unidirectional flow control apparatus shown with flow applied.

FIG. 9 includes a feature of the invention wherein the feature provides a means for ensuring unidirectional flow of Gas Stream A and particulate matter (P of FIGS. 3 and 4) as well as providing a means for automatically sealing the apparatus 10 when the Gas Stream A ceases or the apparatus 10 is removed from the Airflow source (not shown). The feature, a molded, uni-directional flow and sealing apparatus 100, is of a design conducive to injection molding constraints and manufacturing economies. The molded, uni-directional flow and sealing apparatus 100 includes at least one slit 110 to allow Airflow (A of FIG. 4) to pass through as well as sealing the apparatus 10 to entrap the particulate matter P within the mixing chamber 16 while the apparatus is not in use. The function of the molded, uni-directional flow and sealing apparatus 100 is described in detail by FIGS. 10 and 10A.

FIGS. 10 and 10A illustrate the function of the molded, unidirectional flow and sealing apparatus 100. The molded, uni-directional flow and sealing apparatus 100 can be designed to be of a hemispherical shape, whereby the concave side 102 of the unidirectional flow and sealing apparatus 100 would be positioned towards the gas receiving port (26 of FIGS. 5, 6, 7, 8, and 9) of the apparatus 10 and the convex side 104 of the unidirectional flow and sealing apparatus 100 would be positioned towards the gas mixing chamber (16 of FIGS. 5, 6, 7, 8, and 9). The molded, unidirectional flow and sealing apparatus 100 comprising a flexible surface that is portioned into flexible sections 112 by the at least one slit 110. When Gas Stream A is applied to the molded, uni-directional flow and sealing apparatus 100, the Gas Stream A (differential in pressure across the surface) causes flexible sections 112 to elastically bend towards the gas mixing chamber (16 of FIGS. 5, 6, 7, 8, and 9) creating a passage 116 which allows Gas Stream A to pass through the molded, unidirectional flow and sealing apparatus 100 and into the gas mixing chamber 16. When Gas Stream A is removed from the molded, uni-directional flow and sealing apparatus 100, the lack of Gas Stream A (equilibrium in pressure across the surface) allows the flexible sections 112 to elastically return to the natural state of the molded, uni-directional flow and sealing apparatus 100, returning the flexible sections 112 towards the gas receiving port and closing the passage 116 (26 of FIGS. 5, 6, 7, 8, and 9); thus entrapping the particulate matter (P of FIGS. 3 and 4) within the gas mixing chamber 16. The molded, unidirectional flow and sealing apparatus 100 can be molded from a flexible material and stamped to provide the slits 110. The preferred embodiment would be a hemispherical design and include one (1) slit, forming an "I". The hemispherical design provides a geometrical means to limit the motion of the flexible sections 112 during the state lacking Gas Stream A to ensure the flexible sections 112 properly seal.

Method

In practicing the invention, the following method may be used. Reference is once again made to the illustrations of the preferred embodiments, specifically FIG. 4. A stream of gas A is delivered through gas-receiving port 26 and gas-delivery conduit 32 into chamber 16 from the gas air source (not shown). The gas stream A blows through the particulate matter P and causes the particulate matter P, to mix with the gas stream in chamber 16. The air and particle mixture M enter and pass through discharge conduit 28, discharge port 34 and directing tube 36, and exist the apparatus 10 to strike the target material T, this method is performed without generating heat, vibration, appreciable noise levels, and with a device free of any moving pans. In contrast to the prior art devices discussed herein which draw the particulate matter from a reservoir, under vacuum, into a hand piece (and are thus limited as to the amount of pressure that can be exerted an the air/particle stream), the direct blow-through of fluid into the particle mass allows for modulation of the pressure of the resultant stream over a much broader range and thus more precise delivery thereof to a delimited area of a target.

While the various embodiments of the invention have been described and illustrated herein, such is not intended, nor should it be construed a delimiting the scope of the invention, which is set forth in the following claims.

I claim:

1. Handheld apparatus for propelling particulate matter, the apparatus comprising:

a mixing chamber having a sidewall, a gas receiving end wall comprising a gas receiving port at a first end of the mixing chamber and a discharge end wall at an opposite end of the mixing chamber and designed to be handheld;

a gas delivery conduit, whereby the gas delivery conduit would be coupled to the gas receiving end wall and disposed within the mixing chamber and projecting linearly from said gas receiving end wall into the mixing chamber;

a discharge port in the discharge end wall;

a discharge conduit disposed within the mixing chamber and extending in fluid communication from the discharge port towards the gas receiving port and whereby the gas delivery conduit and the discharge conduit overlap;

an elongated particle-directing tube disposed external to the mixing chamber, a proximal end of the particle-directing tube in fluid communication with the discharge port; and the handheld apparatus for propelling particulate matter is pre-charged with a predetermined amount of particulate matter, wherein a maiority of the particulate matter is stored in the mixing chamber, and the handheid apparatus for propelling particulate matter is not conducive for replacing particulate matter, thus providing an apparatus that is designed to be disposed of upon the exhaustion of the particulate matter disposed within the mixing chamber.

2. The apparatus of claim 1, wherein the size and shape of the mixing chamber resembles that of a syringe.

3. The apparatus of claim 1, wherein the elongated particle directing tube is a continuation of the discharge conduit.

4. The apparatus of claim 1, wherein the elongated particle directing tube is manually bendable making the discharge from the elongated particle directing tube omnidirectional at the time of use.

5. The apparatus of claim 1, wherein the apparatus further comprises a color-coding to identify the particulate matter.

6. The apparatus of claim 1, the apparatus further comprising at least one of a gas delivery port cap and a discharge end cap.

7. The apparatus of claim 6, wherein the apparatus further comprising a color-coding to identify the particulate matter.

8. The apparatus of claim 2, the apparatus further comprising an attachment area located proximate the gas receiving port to the apparatus, whereby the attachment area provides a means to couple the apparatus to an air supply source.

9. Handheld apparatus for propelling particulate matter, the apparatus comprising:
a mixing chamber having a sidewall, a gas receiving end wall comprising a gas receiving port at a first end of the mixing chamber and a discharge end wall at an opposite end of the mixing chamber, a coupling member for coupling the mixing chamber to a gas supply source tube, and designed to be handheld;
a gas delivery conduit, whereby the gas delivery conduit would be coupled to the gas receiving end wall and disposed within the mixing chamber and projecting linearly from said gas receiving end wall into the mixing chamber;
a discharge port in the discharge end wall;
a discharge conduit disposed within the mixing chamber and extending in fluid communication from the discharge port towards the gas receiving port and whereby the gas delivery conduit and the discharge conduit overlap;
an elongated particle-directing tube disposed external to the mixing chamber, a proximal end of the particle-directing tube in fluid communication with the discharge port; and
the handheld apparatus for propelling particulate matter is pre-charged with a predetermined amount of particulate matter, wherein a majority of the particulate matter is stored in the mixing chamber, and wherein the handheld apparatus for propelling particulate matter is not conducive to the replenishment of particulate matter, thus providing an apparatus that is designed to be disposed of upon the exhaustion of the particulate matter disposed within the mixing chamber.

10. The apparatus of claim 9, whereby the gas delivery port is positioned off-center with respects to the center of the mixing chamber.

11. The apparatus of claim 9, wherein the size and shape of the mixing chamber resembles that of a syringe.

12. The apparatus of claim 9, wherein the elongated particle directing tube is a continuation of the discharge conduit.

13. The apparatus of claim 9, wherein the elongated particle directing tube is manually bendable making the discharge from the elongated particle directing tube omnidirectional at the time of use.

14. The apparatus of claim 9, wherein me apparatus further comprises a color-coding to identify the particulate matter.

15. The apparatus of claim 9, the apparatus further comprising at least one of a gas delivery port cap and a discharge end cap.

16. The apparatus of claim 15, wherein the apparatus further comprising a color-coding to identify the particulate matter.

17. The apparatus of claim 11, the apparatus further comprising an attachment area located proximate the gas receiving port to the apparatus, whereby the attachment area provides a means to couple the apparatus to an air supply source.

18. Handheld apparatus for propelling particulate matter, the apparatus comprising:
a mixing chamber having a sidewall, a gas receiving port at a first end of the mixing chamber and a discharge end wail at an opposite end of the mixing chamber and designed to be handheld;
a discharge port in the discharge end wall;
a discharge conduit disposed within the mixing chamber and extending in fluid communication from the discharge port towards the gas receiving port;
an elongated particle-directing tube disposed external to the mixing chamber, a proximal end of the particle-directing tube in fluid communication with the discharge port;
a non-removable, self sealing mechanism contiguous to the sidewall of the mixing chamber, wherein the self sealing mechanism opens to allow a gas stream to flow into the handheld mixing chamber when exposed to a gas stream, and the self sealing mechanism seals when not exposed to the gas stream, whereby the self sealing mechanism is located between me gas receiving port and me mixing chamber; and wherein the self-sealing mechanism is of a flexible material, of a hemispherical geometry, and comprising at least two slits.

19. The apparatus of claim 18, wherein the size and shape of the mixing chamber resembles that of a syringe.

20. The apparatus of claim 18, wherein the elongated particle directing tube is a continuation of the discharge conduit.

21. The apparatus of claim 18, wherein the elongated particle directing tube is manually bendable making the discharge from the elongated particle directing tube omnidirectional at the time of use.

22. Handheid apparatus for propelling particulate matter, the apparatus comprising:
a mixing chamber having a sidewall, a gas receiving end wall comprising a gas receiving port at a first end of the mixing chamber and a discharge end wail at an opposite end of the mixing chamber and designed to be handheld;
a gas delivery conduit, whereby the gas delivery conduit would be coupled to the gas receiving end wall and disposed within the mixing chamber and projecting linearly from said gas receiving end wall into the mixing chamber;
a discharge port in the discharge end wall;
a discharge conduit disposed within the mixing chamber and extending in fluid communication from me discharge port towards the gas receiving port and whereby the gas delivery conduit and the discharge conduit overlap;
an elongated particle-directing tube disposed external to the mixing chamber, a proximal end of the particle-directing tube in fluid communication with the discharge port;

the handheld apparatus for propelling particulate matter is pre-charged with a predetermined amount of particulate matter, wherein a majority of the particulate matter is stored in the mixing chamber, and wherein the handheld apparatus for propelling particulate matter is not conducive to the replenishment of particulate matter, thus providing an apparatus that is designed to be disposed of upon the exhaustion of the particulate matter disposed within the mixing chamber, a removable sealing member to temporarily contain the particulate matter within the mixing chamber; and wherein:

at least one of the gas receiving end wall and the discharge end wall abuts and is contiguous with the sidewall of the mixing chamber.

23. The apparatus of claim 22, whereby the gas delivery port is positioned off-center with respects to the center of the mixing chamber.

24. The apparatus of claim 22, wherein the size and shape of the mixing chamber resembles that of a syringe.

25. The apparatus of claim 22, wherein the elongated particle directing tube is a continuation of the discharge conduit.

26. The apparatus of claim 22, wherein the elongated particle directing tube is manually bendable making the discharge from the elongated particle directing tube omni-directional at the time of use.

27. The apparatus of claim 22, wherein the apparatus further comprises a color-coding to identify the particulate matter.

28. The apparatus of claim 22, wherein the removable sealing member to temporarily contain the particulate matter is of at least one of a gas delivery port cap and a discharge end cap.

29. The apparatus of claim 28, wherein the apparatus further comprising a color-coding to identify the particulate matter.

30. The apparatus of claim 24, the apparatus further comprising an attachment area located proximate the gas receiving port to the apparatus, whereby the attachment area provides a means to couple the apparatus to an air supply source.

31. The apparatus of claim 18, the mixing chamber being pre-charged with a particulate matter providing a disposable apparatus upon the exhaustion of me particulate matter disposed within the mixing chamber.

32. The apparatus of claim 18, wherein the at least two slits cross.

33. The apparatus of claim 18, wherein the apparatus further comprises a color-coding to identify the particulate matter.

* * * * *